US009689884B2

(12) United States Patent
Peetz et al.

(10) Patent No.: US 9,689,884 B2
(45) Date of Patent: Jun. 27, 2017

(54) PIPETTING MACHINE HAVING A DISPOSAL CONTAINER

(71) Applicant: HAMILTON BONADUZ AG, Bonaduz (CH)

(72) Inventors: Torsten Peetz, Chur (CH); Andreas Städler, Felsberg (CH)

(73) Assignee: Hamilton Bonaduz AG, Bonaduz (CH)

( * ) Notice: Subject to any disclaimer, the term of this patent is extended or adjusted under 35 U.S.C. 154(b) by 0 days.

(21) Appl. No.: 14/387,896

(22) PCT Filed: Apr. 14, 2013

(86) PCT No.: PCT/EP2013/057749
§ 371 (c)(1),
(2) Date: Sep. 25, 2014

(87) PCT Pub. No.: WO2013/156418
PCT Pub. Date: Oct. 24, 2013

(65) Prior Publication Data
US 2015/0044111 A1 Feb. 12, 2015

(30) Foreign Application Priority Data

Apr. 17, 2012 (DE) .......................... 10 2012 206 239

(51) Int. Cl.
*G01N 35/10* (2006.01)
*B01L 9/00* (2006.01)

(52) U.S. Cl.
CPC .......... *G01N 35/1074* (2013.01); *B01L 9/543* (2013.01); *G01N 2035/103* (2013.01)

(58) Field of Classification Search
CPC .. B01L 9/543; B01L 3/508; B01L 2300/0609;
B01L 2300/0848;
(Continued)

(56) References Cited

U.S. PATENT DOCUMENTS 6,182,719 B1 * 2/2001 Yahiro .................... B01L 9/543
141/1
6,358,470 B1 3/2002 Higuchi
(Continued)

FOREIGN PATENT DOCUMENTS

CN 2762135 Y 3/2006
DE 34 27 679 A1 2/1985
(Continued)

OTHER PUBLICATIONS

International Search Report cited in PCT/EP2013/057749, dated Sep. 9, 2013, 3 pgs.
(Continued)

*Primary Examiner* — Brian R Gordon
(74) *Attorney, Agent, or Firm* — Rothwell, Figg, Ernst & Manbeck, P.C.

(57) ABSTRACT

A metering apparatus includes a base and a vertical support coupled to the base and extending upwardly from the base. The metering apparatus also includes a transverse support coupled to the vertical support, vertically spaced from the base. The metering apparatus also includes a pipetting device coupled to the transverse support, the pipetting device including at least one pipetting channel configured to attach to a pipetting tip. The metering apparatus also includes a disposal container configured to receive used pipetting tips from the pipetting channel, detachably coupled to the vertical support. The pipetting device is movable in first, second, and third directions substantially orthogonal to each other. The disposal container is moveable in one of the first, second, and third directions.

22 Claims, 5 Drawing Sheets

(58) Field of Classification Search
CPC ....... G01N 35/1002; G01N 2035/1032; G01N 2035/1034; G01N 2035/103; G01N 35/1074
See application file for complete search history.

(56) References Cited

U.S. PATENT DOCUMENTS

| | | | |
|---|---|---|---|
| 2001/0005489 A1 | 6/2001 | Roach et al. | |
| 2004/0108330 A1 | 6/2004 | Itoh | |
| 2005/0150314 A1 | 7/2005 | Staples et al. | |
| 2007/0108213 A1* | 5/2007 | Schmidt | B65D 85/24 220/476 |
| 2007/0269343 A1 | 11/2007 | Higuchi et al. | |
| 2010/0229659 A1* | 9/2010 | Ikushima | G01N 35/1011 73/864.11 |

FOREIGN PATENT DOCUMENTS

| | | |
|---|---|---|
| DE | 197 34 129 A1 | 2/1999 |
| DE | 102 45 961 A1 | 4/2004 |
| DE | 29 924 635 U1 | 6/2004 |
| DE | 20 2004 018 586 U1 | 3/2005 |
| DE | 103 48 603 A1 | 5/2005 |
| DE | 699 34 506 T2 | 9/2007 |
| DE | 10 2007 021 952 A1 | 11/2007 |
| DE | 60 2004 004 955 T2 | 12/2007 |
| DE | 10 2008 010 267 A1 | 8/2009 |
| DE | 20 2006 020 707 U1 | 8/2009 |
| EP | 0 114 686 A2 | 8/1984 |
| EP | 1832880 A2 | 9/2007 |
| JP | H11287810 A | 10/1999 |
| JP | 2011059012 A | 3/2011 |

OTHER PUBLICATIONS

Search Report of the German Priority Application No. 10 2012 206 239.4 dated Jan. 23, 2014, 4 pgs.
German Search Report issued in Application No. 10 2012 206 239.4, Apr. 17, 2012, 5 pages.
International Search Report and Written Opinion issued in Application No. PCT/EP2013/057749, issued Oct. 9, 2013, 13 pages.
English Translation of Chinese Office Action for 013800206652, dated Jun. 30, 2015 and Search Report dated Jun. 19, 2015, 18 pages.

\* cited by examiner

PIPETTING MACHINE HAVING A DISPOSAL CONTAINER

CROSS REFERENCE TO RELATED APPLICATION

This application is a 35 U.S.C. 371 National Phase Entry Application from PCT/EP2013/057749 filed Apr. 14, 2013, which claims the benefit of German Patent Application No. 10 201 2 206 239.4 filed on Apr. 17, 2012, the disclosures of which are incorporated herein in their entirety by reference.

BACKGROUND OF THE INVENTION

Field of the Invention

The present invention concerns a metering apparatus, in particular a pipetting machine, comprising a pipetting device moveably in three directions (X, Y, Z) orthogonal to each other with at least one pipetting channel at which a pipetting tip is or can be attached detachably to aspirate sample liquid from a sample container corresponding to the metering apparatus or to dispense sample liquid in a sample container, wherein the at least one pipetting channel is configured such that a pipetting tip detachably attached to it can be removed from the pipetting channel, preferably it can be removed automatically, and a disposal container arranged at the metering apparatus, into which used pipetting tips can be accommodated after removing from a respective pipetting channel.

Background of the Related Art

In known metering apparatuses, in particular pipetting machines, the disposal container is in general arranged at a specific position of the metering apparatus in a fixed manner. The disposal container may for example be designed in form of a bag arranged at the metering apparatus, into which the used pipetting tips are dropped. Such a stationary disposal container is approached after each pipetting process separately by a delivering movement of the pipetting device. Consecutively, a movement of the pipetting device to a supply container for pipetting tips provided at the metering apparatus is carried out to collect clean pipetting tips for the next pipetting process. Removing of the used pipetting tips from the respective pipetting channels is therefore always carried out at the end of the separate delivering movement to the disposal container. The movement of the pipetting device to the disposal container and from the disposal container to the supply container for pipetting tips consumes time and leads to a longer duration of a whole pipetting process, wherein several pipetting processes are executed automatically one after another.

With pipetting tips, which have a length that is a large multiple of their maximal diameter, for example approximately 5 to 25 times, inside the known disposal container a random and disposal volume wasting arrangement of pipetting tips results within the known disposal containers. The reason therefore is that the pipetting tips are accommodated arbitrarily oriented inside of the disposal container, wherein the pipetting tips align under influence of gravity and under influence of colliding with already disposed pipetting tips randomly. Therefore, within the disposal container a chaotic arrangement of used pipetting tips results.

SUMMARY OF THE INVENTION

It is an object of the invention to provide a metering apparatus with disposal container which makes it is possible to avoid the aforementioned disadvantages.

To this end, according to a first aspect it is proposed that the disposal container is arranged at the metering apparatus moveably with respect to the at least one sample container along at least one direction, wherein the pipetting device and the disposal container are at least temporarily moveably in the same direction, preferably synchronously.

Due to the movability of the disposal container in at least one direction it is possible that disposal of pipetting tips, in particular their removal from respective pipetting channels, is carried out during a movement of the pipetting device in this direction(s). Thus, for example already during disposal of the used pipetting tips a movement with regard to a next pipetting process may be performed, wherein simultaneously the disposal process for the used pipetting tips is carried out. By this a path optimization and hence also a time saving in carrying out single pipetting processes of the whole pipetting process results.

Preferably, the sample container are arranged in a pipetting region of a receiving plate of the metering apparatus, wherein the receiving plate is arranged in a plane defined by a first and a second direction (X, Y) and is preferably aligned essentially horizontally, and wherein the pipetting device and the disposal container are moveably relative to the receiving plate.

According to a preferred design the disposal container is moveable along an edge of the receiving plate, wherein the edge runs preferably parallel to the first direction (X).

According to further examples it is proposed that the pipetting device comprises a vertical support aligned essentially orthogonal to the receiving plate, which is moveable along the first direction (X), preferably by means of a motor drive unit, in particular a linear motor, electric motor with gear or the like.

The disposal container is or can be attached to the vertical support, wherein the vertical support and the disposal container are in the attached position detachably connected to each other, preferably such that the vertical support and the disposal container perform coupled movement.

It is further proposed that the disposal container is arranged with respect to the second direction between the vertical support and the pipetting region of the receiving plate.

The disposal container may further be moveable with respect to the pipetting device, in particular with respect to the vertical support in at least one direction, preferably the first direction (X), to be able to bring the disposal container in a desired position at the pipetting device, in particular to a desired relative position to the vertical support. Such a relative movement of the disposal container superposed to the common movement of the disposal container and the vertical support allows also a desired positioning of the disposal container relative to the pipetting channels, from which the pipetting tips fall into the disposal container. Further, such a relative movability of the disposal container may also be advantageous in the regard that the disposal container may be moved automatically into a removal or discharging position, where it may, for example by an operating person, be removed from the pipetting device or where it may be discharged automatically.

According to a second aspect of the invention, which can be self-contained as well as a further development, it is proposed that the disposal container is formed such that the pipetting tips accommodated therein are or become arranged aligned inside the disposal container after removal from a respective pipetting channel.

An aligned arrangement of used pipetting tips in the disposal container allows accommodating a larger number of pipetting tips in comparison with a random arrangement. The moveable disposal container may, due to the constructive basic conditions of the pipetting device, in principle not have an arbitrary form or size. It is therefore particularly preferable, if the usable disposal volume inside the disposal container can be used optimized. An aligned arrangement of pipetting tips is in particular then of great advantage, if the pipetting tips have a clearly elongate form, i.e. if their total length is a multiple of their maximal diameter, wherein for example a length may be assumed, which is about 5 to 25 times the maximal diameter.

To support an alignment of the pipetting tips falling into the disposal container it is proposed that inside the disposal container at least one guiding element is provided, which is formed such that pipetting tips falling from the at least one pipetting channel into the disposal container are or become arranged aligned in the disposal container due to influence of the at least one guiding element and gravity, wherein the pipetting tips are or become arranged preferably lying next to each other and above each other on their peripheral surface. Preferably, the influence of the at least one guiding element and gravity has the effect that the pipetting tips may essentially be arranged or stapled aligned in parallel to each other and next to or above each other.

The disposal container has preferably a receiving opening, which faces in the position attached at the pipetting device the at least one pipetting channel, and through which pipetting tips to be accommodated inside the disposal container fall. The disposal container may have a bottom wall, a first and a second sidewall connected to the bottom wall as well as a first and a second front wall connected with the bottom wall and the sidewalls, wherein the upper edges of the sidewalls and the front walls delimit the receiving opening.

As further example it is proposed that below the receiving opening a first guiding element is arranged inside the disposal container, which is formed by an inclined first collision surface. The first collision surface may extend from the first sidewall of the disposal container in direction to the second sidewall and in direction to both front walls, wherein between the two sidewalls and an edge of the first collision surface facing the second sidewall a free space is formed through which pipetting tips deflected at the first collision surface may fall.

Due to the arrangement of the first collision surface below the receiving opening it is possible to guarantee that a collision of a pipetting tip to be disposed happens such that the probability of a collision with the upper edge of the side and front walls is minimized such that the pipetting tip can arrive safely into a disposal container. The inclination of the first collision surface may be chosen such that a pipetting tip falling down essentially along the vertical direction collides under a specific angle with the collision surface and is deflected in this manner in a desired direction with regard to the aimed at aligned arrangement of the pipetting tip.

It is particularly preferred that the first collision surface is formed with respect to a plane defined by the bottom wall preferably inclined with respect to both main directions of the bottom wall plane, wherein preferably the bottom wall plane forms a parallel plane to the plane defined by the first and second directions (X, Y) or the receiving plate, if the disposal container is attached to the metering apparatus. Such an inclination in two directions has the effect that a down falling pipetting tip is deflected after impact of its tip on the first collision surface purposefully such that it is brought from a essentially vertical alignment in an essentially horizontal position, wherein it may collide with its peripheral surface at the collision surface and slide along this surface towards the free space.

To improve the alignment of pipetting tips further it is proposed that below the first collision surface, in particular below the free space at least one further guiding element is formed, which is preferably formed as inclined further collision surface, wherein preferably the first and the at least one further collision surface are arranged in a cascading manner alternately at the first and the second sidewall. A pipetting tip brought by the first collision surface in an essentially horizontal position may thus fall through the free space and hit onto the further guiding element and is deflected therefrom according to the inclination of its collision surface in a desired direction such that due to the interplay of the several guiding elements the alignment of the down falling pipetting tips may be achieved with great certainty.

In a front wall of the disposal container may be provided at least one discharge opening through which pipetting tips accommodated inside the disposal container are removable from the disposal container. To this end it is further proposed that in the respective front wall two discharge openings arranged above each other are provided, wherein preferably the guiding element inside the disposal container are arranged such that pipetting tips accommodated in the disposal container are moved at a specific discharge position of the disposal container under influence of the guiding elements and gravity in direction to the discharge openings. The arrangement and inclination of the several guiding elements is therefore not only advantageous for the aligned arrangement of the pipetting tips, but it allows also a simple and complete discharging of the disposal container.

According to a third aspect of the invention a disposal container is proposed for elongate, at least in sections cylindrically formed objects, in particular pipetting tips of a metering apparatus, as for example hand pipettes or pipetting machines, with a receiving opening through which objects to be accommodated inside the disposal container fall, characterized in that the disposal container is formed such that objects accommodated inside the disposal container are or become arranged aligned, wherein preferably at least one guiding element is provided in the disposal container, which is formed such that objects falling into the disposal container are or become arranged aligned inside the disposal container under influence of the at least one guiding element and gravity, wherein the objects are or become preferably arranged lying on their peripheral surface next to each other or above each other inside the disposal container.

Such a disposal container may therefore not only be used for pipetting tips as preferred objects, but also for other elongate articles, as for example syringes, capillary tubes and the like. In this process, the object to be disposed may also be dropped manually by a person into the disposal container.

Such a disposal container may at least comprise a further feature corresponding to the disposal container according to the above description, irrespective, if it is used in one of the above described metering apparatuses.

BRIEF DESCRIPTION OF THE DRAWINGS

In the following the invention will be described exemplarily and non-limiting with respect to an embodiment.

DETAILED DESCRIPTION

Figure 1:
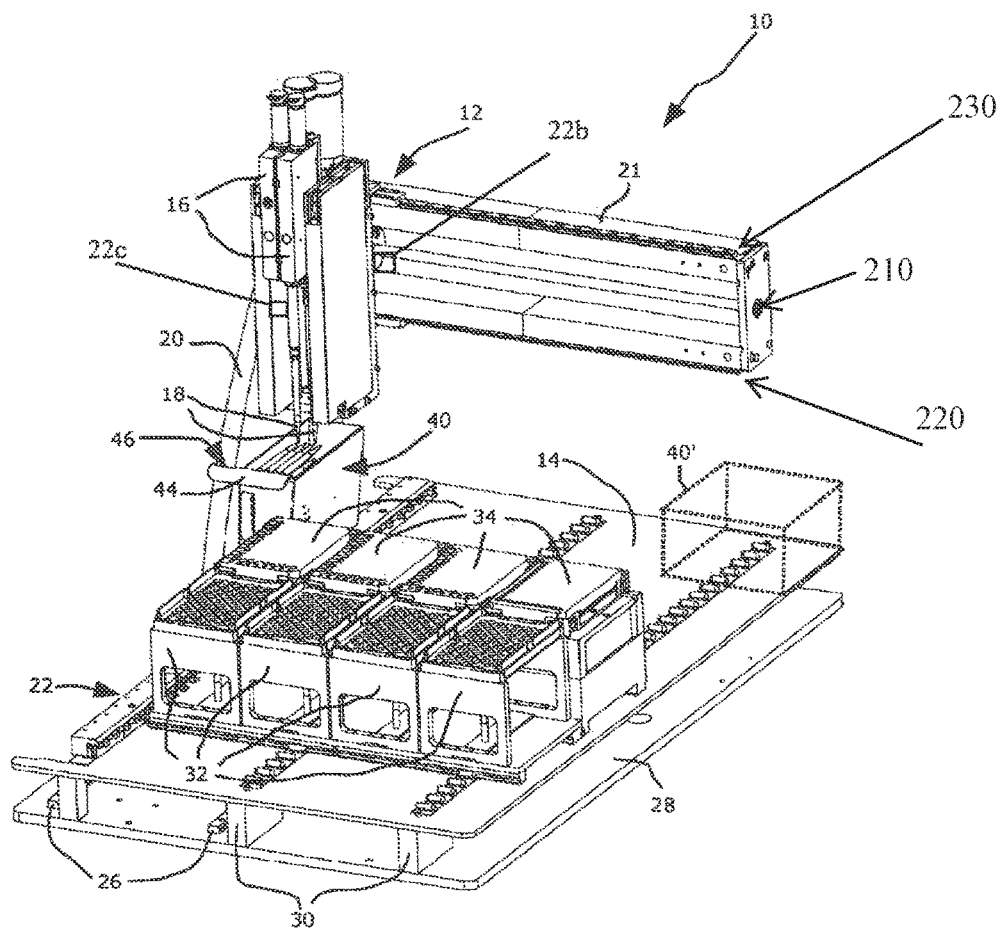
FIG. 1 shows in simplified schematic perspective view an embodiment of a metering apparatus with disposal container.
Figure 1:
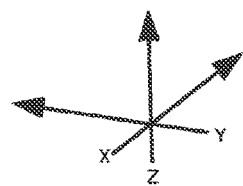
Figure 2:
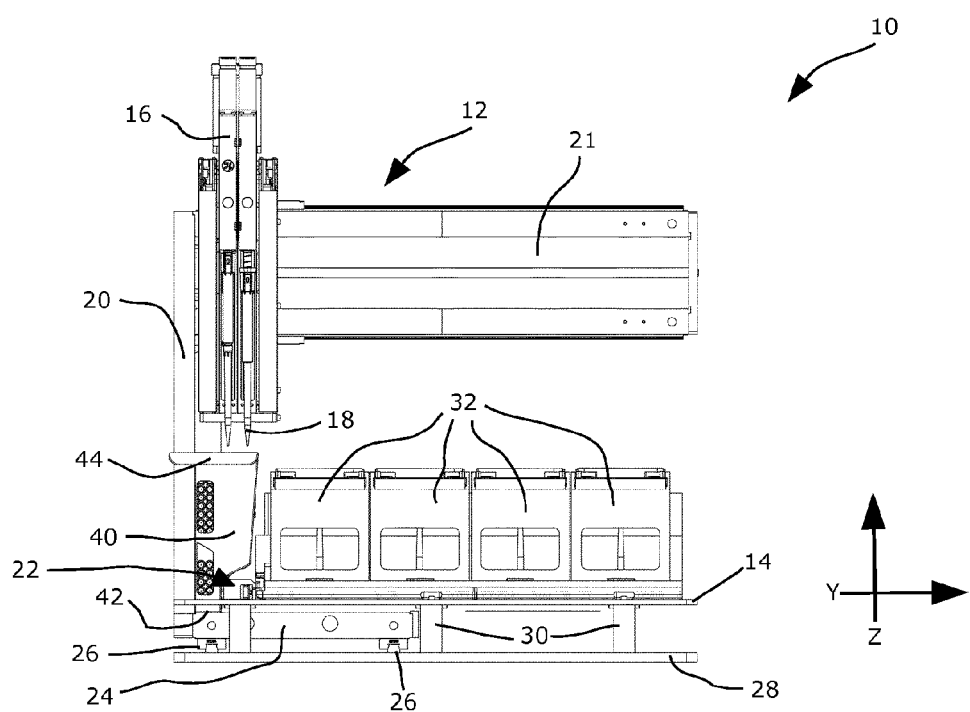
FIG. 2 shows the metering apparatus of FIG. 1 in a front view in a first direction (X).
Figure 3:
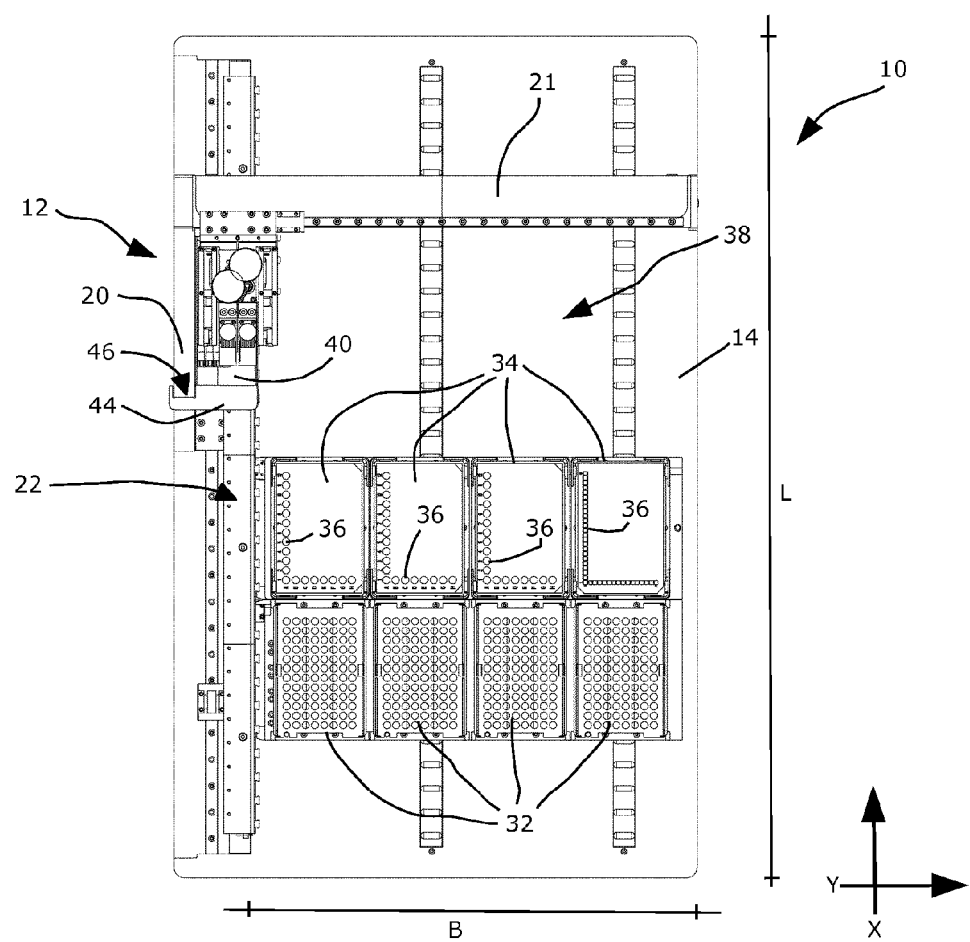
FIG. 3 shows the metering apparatus of FIG. 1 as top view from a further direction (Z).

From the synopsis of FIGS. 1 to 3 a metering apparatus 10 with a pipetting device 12 can be seen. The pipetting device 12 is formed moveably relative to a receiving plate 14 of the metering apparatus, wherein by means of the pipetting device 12 pipetting channels 16 and pipetting tips 18 attached thereon may be moved in three directions X, Y and Z orthogonal to each other. Along the X direction the movement of the pipetting device 12 is carried out by means of a vertical support 20 arranged at the receiving plate 14. The vertical support is movable in the X direction along the edge of the receiving plate 14, preferably by means of a motor drive and a corresponding linear guidance. In the present embodiment the vertical support 20 is driven by a linear motor, which is indicated by reference numeral 22. The vertical support 20 has a bearing support 24 essentially aligned horizontally, which rests on two guiding rails 26. The guiding rails are connected with a support plate 28 arranged in parallel to the receiving plate 14. The receiving plate 14 is arranged above the support plate 28 and is connected with it via bearer-like supporters 30. In an upper section of the vertical support 20 a transverse support 21 is attached, along which the pipetting channels 16 may move along the Y direction by means of an according driving unit, such as a motor with gear (e.g., motor with gear 210, with lower guiding rails 220 and upper guiding rails 230), linear motor and the like (e.g., motor drive and linear guidance 22b). The pipetting channels 16 and if applicable pipetting tips 18 attached to it are finally moveable in the Z direction by means of an according further drive, such as a spindle drive or the like (e.g., motor drive and linear guidance 22c).

On the receiving plate 14 pipetting tip containers 32 are arranged, which serve as supply container or reservoirs for unused pipetting tips 18. Further, by reference sign 34 sample containers are indicated, by which sample liquid to be analyzed may be accommodated in according recesses 36. Using the pipetting channels 16 and the pipetting tips 18 attached thereon sample liquid may be taken out (aspirated) from the recesses 36 of the sample container 34 and delivered (dispensed) into other recesses 36 of the same or of another sample container 34. The region of the receiving plate 14 on which pipetting tip container 32 or/and sample container or/and further working materials or working devices possible for such a metering apparatus 10 may be arranged, is designated here as pipetting region 38 with a length extension L in X direction and a transverse extension B in Y direction (FIG. 3).

As can be seen particularly from FIGS. 1 and 2 on the vertical support 20 a disposal container 40 is provided. This disposal container 40 is connected detachably with the vertical support 20. To this end, the detachable connection between the disposal container 40 and the vertical support 20 is formed such that the disposal container 40 may be moved with the vertical support 20 in the X direction. In the present embodiment the disposal container 40 is supported by its bottom wall 42 from the bearing support 24. In particular, the disposal container may be accommodated with its lower region 25 (FIGS. 4 and 6), which is located upwards and adjacent to the bottom wall 42, in a corresponding holder on the vertical support 20 or its bearing support 24. In the area of a contact region of the disposal container 40 a contact with the vertical support 20 is formed by means of a recess 46 formed in the contact region 44. This contact in the region of the recess 46 leads to an improved fixation of the disposal container 40 to the vertical support 20, in particular due to this, tipping of the disposal container 40 into the Y direction, i.e. traversal to the movement direction of the vertical support 20 and the disposal container 40 coupled to it, is prevented.

According to a not illustrated alternative the disposal container 40 may for example be attached to the vertical support 20 such that it may be additionally moved along the X direction also relative to the vertical support 20 such that the disposal container 40 may be arranged at varying relative positions with respect to the vertical support 20 and may be kept at these positions if necessary. Further, it is possible that the disposal container 40 is movable in further directions with respect to the vertical support 20, in particular by means of respective drives and holders such that also an automated exchange or/and discharge of the disposal container may be conceivable. Attaching the disposal container 40 to the vertical support 20 may also be carried out in differing manner, wherein the main focus is that the disposal container performs at least temporarily coupled movement with the vertical support 20, in particular during pipetting processes.

The functioning of the metering apparatus 10 with the moveable disposal container will be explained briefly in the following. At the beginning of a pipetting process new pipetting tips 18 are retrieved by the pipetting channels 16 from the pipetting tip container 32 and coupled to the pipetting channels. Consecutively, movement of the pipetting channels 16 and the pipetting tips 18 attached thereto to a desired sample container 34 is carried out, in particular to the desired recesses 36 from which sample liquid is aspired. The pipetting tips 18 filled with sample liquid are then moved for example to a different sample container and in particular to different recesses 36 such that the collected sample liquid may be dispensed into these recesses 36. Obviously, it is also possible that aspirated sample liquid may be dispensed or distributed consecutively in small amounts into several recesses 36. After finishing of the dispensing the pipetting channels 16 and the used pipetting tips 18 provided thereon may be moved in the direction of the disposal container 40. As soon as the pipetting channels 16 have arrived at a desired Y position, which corresponds to a Y position of the disposal container 40, the used pipetting tips 18 may be removed from the pipetting channels and drop because of gravity downwards into the disposal container 40. This removal process between pipetting tips 18 and pipetting channels 16 may be carried out at the aforementioned Y position also then, if the pipetting device 12 is already moved into the X direction again, in particular in direction to the pipetting tip container 32. The disposal of the used pipetting tips 18 is therefore carried out during a movement of the pipetting device 12, which has to be carried out during the pipetting process or during preparation of a next pipetting process anyway, to fetch again unused pipetting tips 18 from the pipetting tip container 32. Due to this process the necessary overall movement during a pipetting process can be reduced in comparison with an arrangement, in which a disposal container 40' is arranged stationary in the area of the receiving plate 14, for example as indicated in FIG. 1 by the broken lines in the lower right corner of the receiving plate 14.

With reference to FIGS. 4 to 8 the disposal container 40 is described in more detail in the following, in particular with regard to the aligned arrangement of used pipetting tips 18. The disposal container 40 has a bottom wall 42 as well as a first and a second sidewall 48 and 50, which are connected with the bottom wall 42. The sidewalls 48, 50 are connected to each other by a first and a second front wall 52 and 54. In the embodiment the contact region 44 is arranged at the first front wall 52. Such an arrangement of the contact region 44 or another type of handle is, however, not to be understood limiting. A handle may also be provided at the second front wall 54 or at one of the sidewalls 48, 50. Further, it is also conceivable that more than one handle or contact region are provided.

The upper edges of the sidewalls 48, 50 and the front walls 52, 54 delimit a receiving opening 56 through which pipetting tips 18 may fall into the disposal container 40. Normally, the pipetting tips 18 falling into the disposal container 40 will be essentially aligned in vertical direction (Z direction) as they are attached in such an alignment to the pipetting channels 16 (FIG. 1).

Inside the disposal container 40 a first guiding element 58 is arranged below the receiving opening 56 (FIGS. 7 and 8), which may be formed in form of an inclined collision surface. The first guiding element 58 is preferably inclined into two directions, in particular such that the collision surface has an inclination leading from the first to the second front wall 52, 54 and from the first to the second sidewall 48, 50 downwards into the interior of the disposal container 40. Taking the bottom wall 42 as a reference plane, the collision surface 58 is formed with respect to the main directions of the bottom wall plane inclined with respect to both main directions. The collision surface 58 inclined into two direction has the effect that a pipetting tip normally impinging with its tip 60 first is deflected in direction to the second front wall 54 and in direction to the second sidewall 50 such that the pipetting tip 18 may be brought from the essentially vertical falling direction at first into an oblique position and later to an essentially horizontal alignment.

The collision surface 58 extends into the direction of the second sidewall a bit beyond the middle of the disposal container such that a free space 62 is formed through which the pipetting tips may fall further downwards. During the passage through this free space a falling pipetting tip becomes due to the influence of the collision surface 58 and the gravity already aligned such that its tip 60 faces the second front wall 54 and it is aligned in an oblique position approximating a horizontal position.

Below the free space 62 a further guiding element 64 may be provided, which extends from the second sidewall 50 inclined into the direction of the interior of the disposal container 40. Preferably, this second guiding element 64, which may also be denoted as second collision surface 64, is inclined only in one direction such that it has starting from the second sidewall 50 a downwardly pointing inclination towards the first sidewall 48. A pipetting tip impinging on this second guiding element 64 will slide along this inclined second collision surface 64 and fall further downwards, by which a further approximation to the desired alignment of the pipetting tip to the essentially horizontal direction may by achieved.

Figure 8:
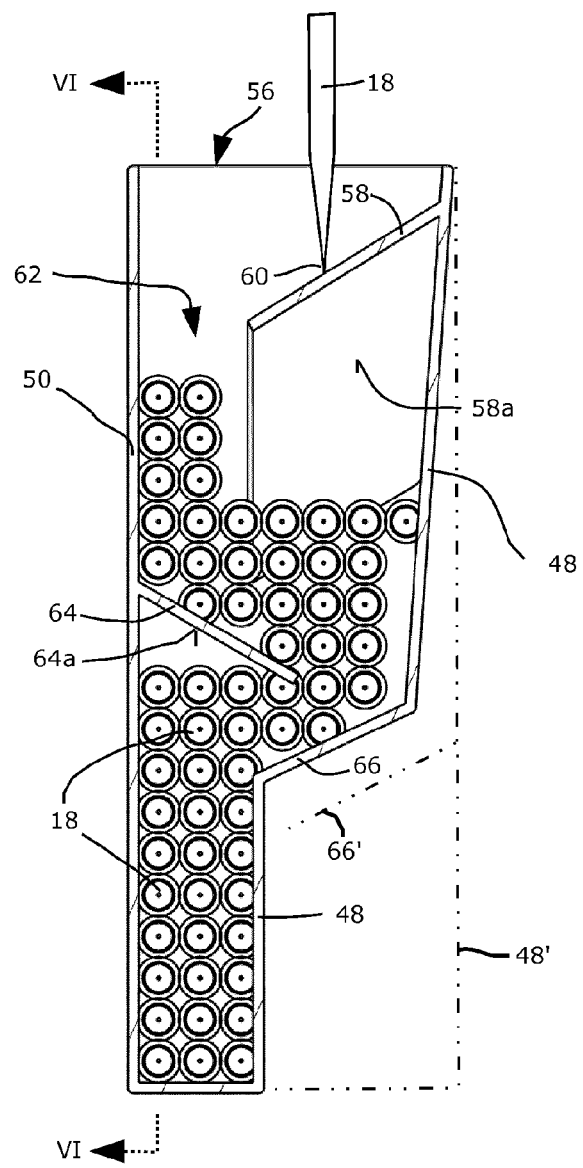
FIG. 8 shows a simplified and schematic sectional view according to the intersecting line VIII-VIII of FIGS. 4 and 7.

In the disposal container 40 exemplarily shown here in connection with a corresponding pipetting device 12 the first sidewall 48 has below the second guiding element 64 an inclined wall region 66 pointing inwards, which may be denoted as further (third) guiding element. Along this third guiding element 66 pipetting tips slide or roll further downwards in direction to the bottom wall 42. An alternative third guiding element 66' may for a first sidewall 48' essentially being straight from top to bottom analogously to the second guiding element 64 also be connected with the first sidewall 48' and protrude in direction of the interior, as is indicated in FIG. 8 by the dashed line. Altogether a kind of cascade of guiding elements 58, 64 and 66 results, which are arranged alternately at sidewalls 48, 50 opposite to each other or is formed by these such that pipetting tips 18 falling into the disposal container 40 may be brought into a desired aligned arrangement.

Such an arrangement of guiding elements with inclined collision surfaces may in general be provided in an arbitrary design of a disposal container. The arrangement and design of the guiding elements may also be provided specifically for the objects to be disposed, wherein the outer form of the disposal container may remain the same. It is for example conceivable that for shorter objects a different arrangement of guiding elements is preferable to achieve a desired alignment of shorter objects.

The disposal container 40, which is, because of the constructive basic conditions of the pipetting device 12, formed tapered towards its bottom, may also comprise two parallel sidewalls such that it is formed rather cuboid-shaped as is indicated by the dashed line in FIG. 8, which represents the first sidewall 48' with the corresponding third guiding elements 66'. In this respect the disposal container and the arrangement of at least one guiding element for aligning elongated objects falling into it is also a self-contained aspect of the invention, independent from the fact whether the disposal container is used for a pipetting machine and for accommodating pipetting tips. Conceivable is also the use as disposal container for pipetting tips, which are removed from a hand pipette. Most general, a disposal container with at least one guiding element as presented here may also be used for alignment of further elongated objects, such as elongated tubes, cylinder-like elongated rods, syringes and the like.

Figure 6:
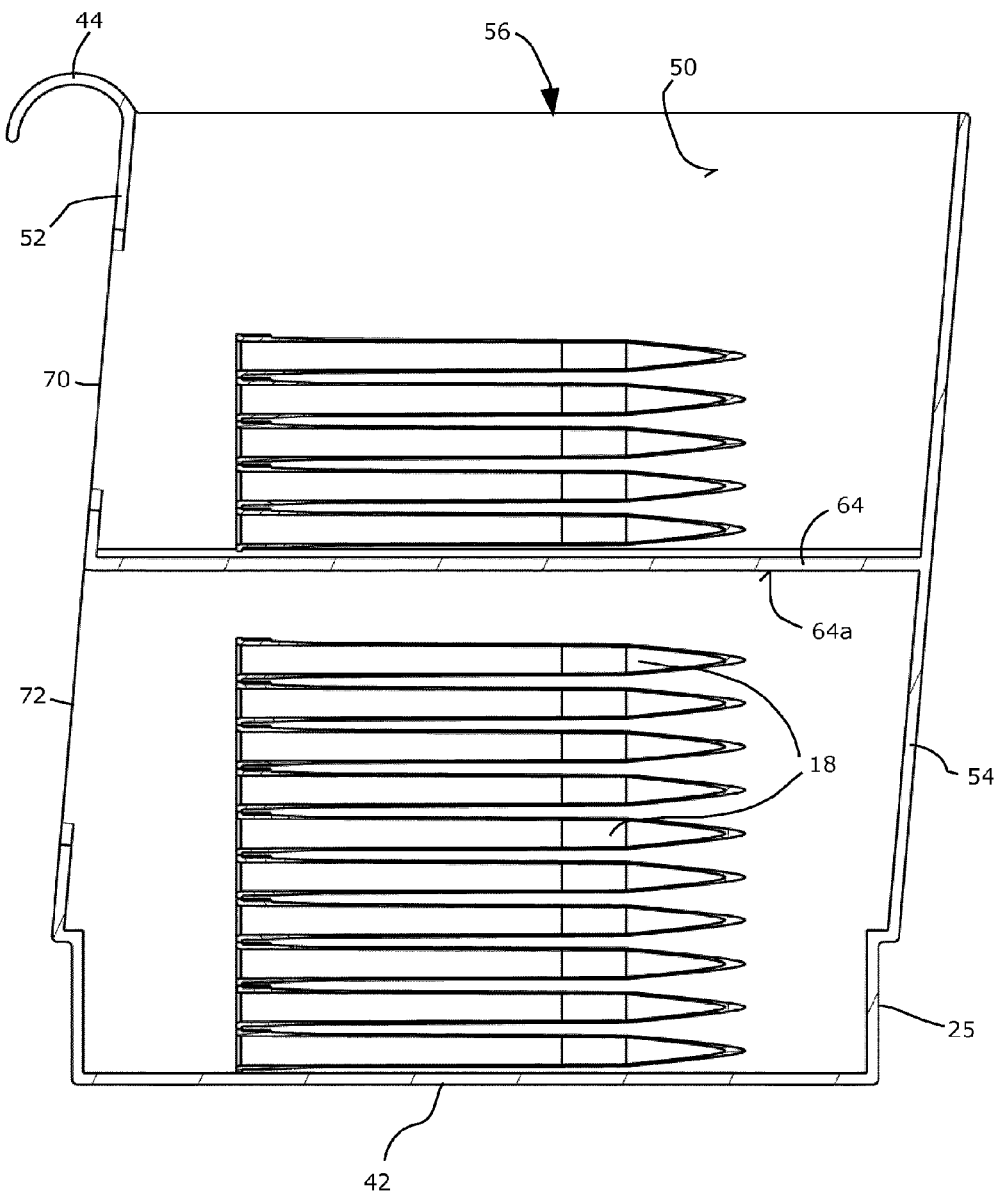
FIG. 6 shows a simplified and schematic sectional view according to the intersecting line VI-VI of FIGS. 4 and 8.
Figure 6:
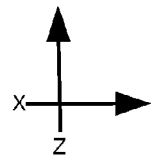
Figure 7:
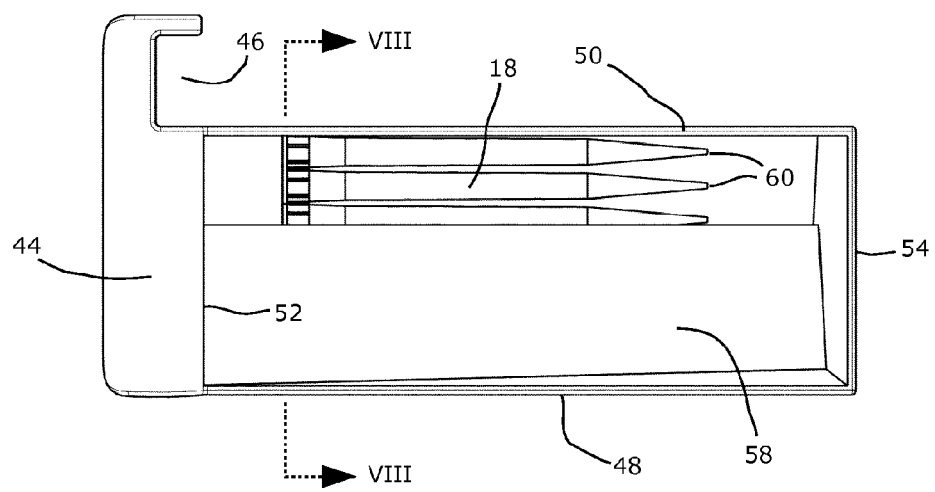
FIG. 7 shows a simplified and schematic top view of a receiving opening of the disposal container of FIG. 4 from a further direction (Z).

The pipetting tips falling into the disposal container 40 or in the general case other elongate, in particular cylindrical objects, are arranged starting from the bottom wall 42 in upward direction on top of each other and next to each other. In FIGS. 6 to 8 a very simplified schematic illustration of the arrangement of pipetting tips 18 has been chosen, in which the pipetting tips are arranged in horizontal rows and vertical columns. However, it may also be the case that the pipetting tips 18 arrange themselves in consecutive rows offset to each other with respect to the columns, in particular such that a pipetting tip of an upper row is adjacent to the peripheral surface of two lower pipetting tips, for example according to the principle of sphere packing applied to the cylindrical form of the pipetting tips.

Figure 4:
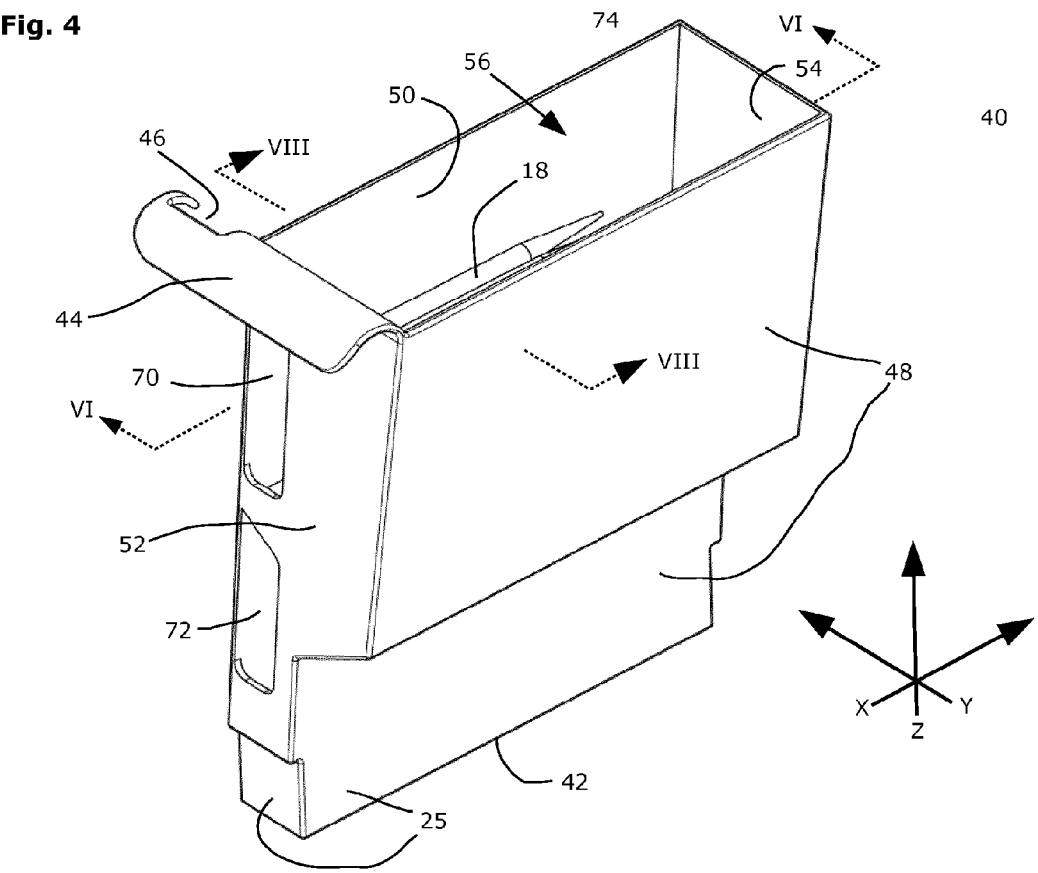
FIG. 4 shows in simplified and schematic illustration an embodiment of a disposal container for the metering apparatus.
Figure 5:
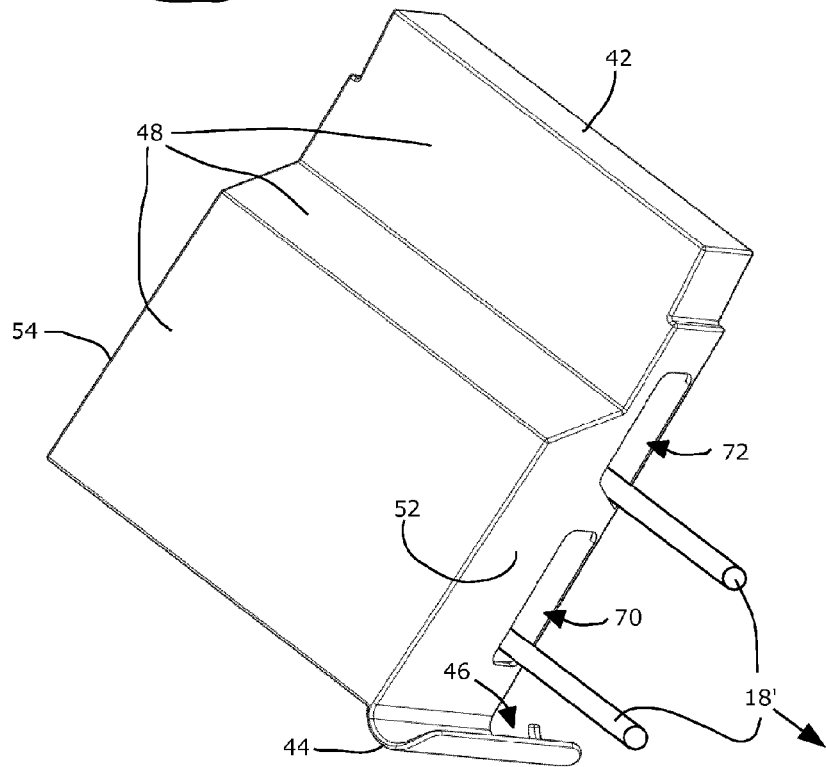
FIG. 5 shows the disposal container in a position suitable for discharging it.

In the first front wall 52 discharge openings 70 and 72 are provided as can be seen from FIGS. 4 to 6. Through these discharge openings 70, 72 pipetting tips 18 accommodated inside the disposal container 40 and arranged aligned may be removed again from the disposal container. To this end, the disposal container 40 may be brought from a position according to FIG. 4 (bottom wall 42 is located at the bottom) in a rotated position according to FIG. 5. In this rotated discharging position according to FIG. 5 the bottom wall 42 faces upwards and is inclined such that pipetting tips contained in the disposal container 40 are moved in direction to the second sidewall 50 and the first front wall 52, in particular in direction to the discharge openings 70, 72, in particular under influence of gravity. Additionally, the pipetting tips 18 accommodated inside the disposal container 4 are moved under influence of the inclined surfaces of the respective reverse sides 58a and 64a (FIG. 8) of the guiding elements 58 and 64 in direction of the discharging openings 70, 72 such that they get through these out of the disposal container 40. Exemplarily this is indicated in FIG. 5 by the two pipetting tips 18' and the arrow of the direction indicated at 18', into which the pipetting tips 18' move out of the discharging opening 70, 72.

It is obviously also conceivable that the discharging openings 70, 72 may be provided at the second front wall 54. This may for example then be advantageous, if in particular an inclination of the first guiding element 58 from the second front wall 54 to the first front wall 52 points downwards (reverse to the illustration according FIGS. 7 and 8) with constant inclination between the two sidewalls 50, 52 (i.e. as illustrated in FIGS. 7 and 8).

Altogether by the design of the disposal container 40 as a moveable element attached on the pipetting device as well as by the aligned arrangement of pipetting tips 18 inside the disposal container 40 an optimized utilization results. The path to be driven by the pipetting device may be optimized, since the disposal of pipetting tips may be performed during a delivering movement along the X direction. Further, the volume of the disposal container may be used optimally such that the disposal container has to be discharged less often or such that a full disposal container has to be replaced less often by an empty one.

The invention claimed is:

1. An automated metering apparatus comprising: a base; a vertical support coupled to the base and extending upwardly from the base; a transverse support coupled to the vertical support, vertically spaced from the base; a pipetting device coupled to the transverse support, the pipetting device including at least one pipetting channel configured to attach to a pipetting tip; and a disposal container configured to receive used pipetting tips from the pipetting channel, said disposal container detachably coupled directly to the vertical support, wherein the pipetting device is movable in first, second, and third directions substantially orthogonal to each other, and wherein the automated metering device is automated to move the disposal container in one of the first, second, and third directions.

2. The metering apparatus of claim 1, wherein the disposal container and the pipetting device are at least temporarily movable in the same direction.

3. The automated metering device of claim 2, wherein the disposal container and the pipetting device are synchronously movable.

4. The automated metering apparatus of claim 1, wherein the base includes:
a receiving plate;
a supporting plate positioned below the receiving plate;
at least one first support coupled between and separating the receiving plate and the supporting plate;
two parallel guide rails on a surface of the supporting plate facing the receiving plate; and
a second support coupled to the vertical support and to the two guide rails, the second support being aligned substantially horizontally in the first direction,
wherein the vertical support is movable in the first direction along the two guide rails.

5. The automated metering apparatus of claim 4, further comprising a first motor drive unit which is operable to move the vertical support and the disposal container in the first direction, wherein the first motor drive unit includes a first motor drive and a first guidance.

6. The automated metering apparatus of claim 5, wherein the first motor drive includes a linear motor.

7. The automated metering apparatus of claim 4, wherein the at least one pipetting channel is movable along the transverse support in the second direction.

8. The automated metering apparatus of claim 7, further comprising a second motor drive unit which is operable to move the at least one pipetting channel in the second direction, wherein the second motor drive unit includes a second motor drive and a second guidance.

9. The automated metering apparatus of claim 7, wherein the at least one pipetting channel is movable in the third direction.

10. The automated metering apparatus of claim 8, further comprising a third motor drive unit which is operable to move the at least one pipetting channel in the third direction, wherein the third motor drive unit includes a third motor drive and a third guidance.

11. The automated metering apparatus of claim 10, wherein the third motor drive includes a spindle drive.

12. The automated metering apparatus of claim 9, further comprising: at least one pipetting tip container coupled to the base; and
a plurality of sample containers coupled to the base, wherein the plurality of sample containers each includes a plurality of recesses configured to accommodate a sample liquid.

13. The automated metering apparatus of claim 12, wherein the disposal container includes:
a bottom wall supported by the second support; first and second sidewalls connected to the bottom wall; first and second front walls connecting the first and second sidewalls, wherein upper edges of the first and second sidewalls and front walls delimit a receiving opening.

14. The automated metering apparatus of claim 13, wherein the disposal container further includes:
a first guiding element positioned below the receiving opening, having an inclined collision surface.

15. The automated metering apparatus of claim 14, wherein the collision surface of the first guiding element includes a first inclination leading from the first to the second front wall and a second inclination leading from the first to the second sidewall.

16. The automated metering apparatus of claim 13, wherein the disposal container further includes:
a second guiding element positioned below the first guiding element, extending from the second sidewall and inclined toward the bottom wall of the disposal container; and
a third guiding element positioned below the second guiding element, comprising an inclined wall region of the first sidewall.

17. The automated metering apparatus of claim 13, wherein the disposal container further includes a first discharge opening in the first sidewall.

18. The automated metering apparatus of claim 17, wherein the disposal container further includes a second discharge opening in the first sidewall vertically spaced from the first discharge opening.

19. A method of using a metering apparatus, the method comprising:
  providing the automated metering apparatus according to claim 13;
  retrieving a pipetting tip with the at least one pipetting channel from the at least one pipetting tip container;
  attaching the pipetting tip to the at least one pipetting channel; moving the at least one pipetting channel to one of the plurality of sample containers;
  filling the pipetting tip with a liquid from the one of the plurality of sample containers; and
  moving the at least one pipetting channel to a different one of the plurality of sample containers.

20. The method of claim 19, further comprising:
  moving the at least one pipetting channel in a position over the disposal container; and
  removing the pipetting tip from the at least one pipetting channel, wherein the pipetting tip drops into the disposal container.

21. The method of claim 20, further comprising:
  moving the disposal container and the pipetting device at least temporarily in the same direction during removing the pipetting tip.

22. The method of claim 21, further comprising:
  moving the disposal container and the pipetting device synchronously.

* * * * *